(12) United States Patent
Ye et al.

(10) Patent No.: US 11,099,189 B2
(45) Date of Patent: Aug. 24, 2021

(54) LIMULUS AMOEBOCYTE LYSATE ASSAY AND METHOD OF SAME

(71) Applicant: BOARD OF REGENTS, THE UNIVERSITY OF TEXAS SYSTEM, Austin, TX (US)

(72) Inventors: Jing Yong Ye, San Antonio, TX (US); Jonathan D. Scudder, San Antonio, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 151 days.

(21) Appl. No.: 16/162,261

(22) Filed: Oct. 16, 2018

(65) Prior Publication Data
US 2019/0113514 A1 Apr. 18, 2019

Related U.S. Application Data

(60) Provisional application No. 62/573,535, filed on Oct. 17, 2017.

(51) Int. Cl.
*G01N 33/579* (2006.01)
*G01N 21/31* (2006.01)
(Continued)

(52) U.S. Cl.
CPC ......... *G01N 33/579* (2013.01); *G01N 21/314* (2013.01); *G01N 21/7743* (2013.01);
(Continued)

(58) Field of Classification Search
CPC ............. G01N 33/579; G01N 2400/50; G01N 33/56911; G01N 21/17; G01N 2333/195;
(Continued)

(56) References Cited

U.S. PATENT DOCUMENTS 5,313,264 A * 5/1994 Ivarsson ............... G01N 21/552
250/458.1
5,605,806 A * 2/1997 Tanaka ................. G01N 33/579
435/7.32

(Continued)

FOREIGN PATENT DOCUMENTS

EP 2041172 11/2013 ........... C07K 14/705

OTHER PUBLICATIONS

Barnett, M.J. et al., In-Field Implementation of a Recombinant Factor C Assay for the Detection of Lipopolysaccharide as a Biomarker of Extant Life within Glacial Environments. Biosensors 2012, 2 (1), 83-100.
(Continued)

*Primary Examiner* — Michael P Stafira
(74) *Attorney, Agent, or Firm* — David G. Rosenbaum; Rosenbaum IP (57) ABSTRACT

A pyrogenicity test assay and method of pyrogen testing that allows for rapid and ultrahigh sensitivity testing of parenteral pharmaceuticals or medical devices that contact blood or cerebrospinal fluid by employing a Limulus Amoebocyte Lysate (LAL) assay utilizing a photonic-crystal biosensor. The photonic-crystal biosensor is capable of determining the presence of endotoxins in a test sample by monitoring shifts in the resonant wavelength of an open microcavity affected by the changes in the refractive index of the analyte solutions used.

8 Claims, 4 Drawing Sheets

(51) Int. Cl.
*G01N 21/77* (2006.01)
*G01N 21/43* (2006.01)

(52) U.S. Cl.
CPC ............... *G01N 2021/3125* (2013.01); *G01N 2021/436* (2013.01); *G01N 2400/50* (2013.01)

(58) Field of Classification Search
CPC ........... G01N 2400/10; G01N 33/6893; G01N 2333/57; G01N 2800/52; G01N 33/574; G01N 33/6866; G01N 33/84; G01N 15/14; G01N 1/38; G01N 2021/3125; G01N 2021/436; G01N 21/314; G01N 21/7743; G01N 21/78; G01N 2333/70503; G01N 2333/70535; G01N 2500/00; G01N 27/22; G01N 2800/12; G01N 2800/26; G01N 33/52; G01N 33/521; G01N 33/53; G01N 33/564; G01N 33/566; G01N 33/569; G01N 33/56916; G01N 33/56972; G01N 33/57484; G01N 33/577; G01N 33/68; G01N 33/6854; G01N 33/92; G01N 21/01; G01N 21/278; G01N 21/4785; G01N 21/6452; G01N 21/648; G01N 21/76; G01N 2201/06113; G01N 2201/0612; G01N 2201/062; G01N 2201/0691; G01N 2201/0697; G01N 21/554; G01N 21/553; G01N 21/6458; G01N 21/658; G01N 2021/058; G01N 2021/8829; G01N 2021/8848; G01N 21/253; G01N 21/4133; G01N 21/55; G01N 21/552; G01N 21/636; G01N 21/6486; G01N 21/65; G01N 21/84; G01N 21/88; G01N 21/8806; G01N 27/04; G01N 33/2823; G01N 33/483; G01N 33/48721; G01N 33/49; G01N 33/54366; G01N 33/54373; G01N 33/551; G01N 33/57449; G01N 21/6456
See application file for complete search history.

(56) References Cited

U.S. PATENT DOCUMENTS

| | | | |
|---|---|---|---|
| 6,696,261 B2 | 2/2004 | Patel et al. | 435/7.24 |
| 7,639,362 B2 | 12/2009 | Ye et al. | 356/445 |
| 8,497,992 B2 | 7/2013 | Ye et al. | 356/448 |
| 9,080,973 B2* | 7/2015 | Abbott | G01N 21/49 |
| 10,620,205 B2* | 4/2020 | Dhanda | G01N 33/573 |
| 2001/0040130 A1* | 11/2001 | Lorch | G01N 21/553 |
| | | | 210/601 |
| 2008/0225293 A1* | 9/2008 | Ye | G02B 1/005 |
| | | | 356/364 |
| 2010/0065732 A1* | 3/2010 | Ye | B82Y 20/00 |
| | | | 250/281 |
| 2012/0015377 A1* | 1/2012 | Hirono | G01N 21/82 |
| | | | 435/7.21 |
| 2012/0100624 A1* | 4/2012 | Hara | G01N 33/5304 |
| | | | 436/94 |
| 2013/0168536 A1* | 7/2013 | Guo | G02B 1/005 |
| | | | 250/216 |
| 2016/0238526 A1* | 8/2016 | Fadaei | G01N 21/553 |
| 2017/0214002 A1* | 7/2017 | Riedel | F21V 7/0016 |
| 2018/0188249 A1 | 7/2018 | Alexander et al. | G01N 33/569 |
| 2020/0158616 A1* | 5/2020 | Knollenberg | G01N 15/02 |

OTHER PUBLICATIONS

Basinas, I. et al., A comprehensive review of levels and determinants of personal exposure to dust and endotoxin in livestock farming. Journal of Exposure Science and Environmental Epidemiology 2015, 25 (2), 123-137.

Breese, G., ASMFC Stock Assessment Overview: Horseshoe Crab. Atlantic States Marine Fisheries Commission: 2010.

Chesler, C., Medical Labs May Be Killing Horseshoe Crabs Scientific American [Online], 2016. https://www.scientificamerican.com/article/medical-labs-may-be-killing-horseshoe-crabs/ (accessed Oct. 15, 2016).

Cooper, J., Atlantic States Marine Fisheries Commission http://www.asmfc.org/species/horseshoe-crab (accessed Nov. 20, 2016).

De Oliveira, L.D. et al., Efficacy of endodontic treatment for endotoxin reduction in primarily infected root canals and evaluation of cytotoxic effects. Journal of endodontics 2012, 38 (8), 1053-1057.

DuBose, D.A. et al., Comparison of plasma extraction techniques in preparation of samples for endotoxin testing by the Limulus amoebocyte lysate test. Journal of clinical microbiology 1980, 11 (1), 68-72.

Dungan, R.S., Airborne endotoxin from indoor and outdoor environments: effect of sample dilution on the kinetic Limulus amebocyte lysate (LAL) assay. Journal of occupational and environmental hygiene 2011, 8 (3), 147-153.

Gnauck, A. et al., The Limulus Amebocyte Lysate assay may be unsuitable for detecting endotoxin in blood of healthy female subjects. Journal of immunological methods 2015, 416, 146-156.

Hartung, T., The Human Whole Blood Pyrogen Test—Lessons Learned in Twenty Years. Altex 2015, 32 (2), 79.

Hwang, S.H. et al., Outdoor (1→3)-β-D-glucan Levels and Related Climatic Factors. Journal of Preventive Medicine and Public Health 2014, 47 (2), 124.

Kobayashi, Y. et al., Factor B is the Second Lipopolysaccharide-binding Protease Zymogen in the Horseshoe Crab Coagulation Cascade. Journal of Biological Chemistry 2015, 290 (31), 19379-19386.

Marinho, A.C. et al., Accuracy of Turbidimetric Limulus Amebocyte Lysate Assay for the Recovery of Endotoxin Interacted with Commonly Used Antimicrobial Agents of Endodontic Therapy. Journal of endodontics 2015, 41 (10), 1653-1659.

Moisan, M. et al., Low-temperature sterilization using gas plasmas: a review of the experiments and an analysis of the inactivation mechanisms. International journal of Pharmaceutics 2001, 226 (1), 1-21.

Novitsky, T.J., Limitations of the Limulus amebocyte lysate test in demonstrating circulating lipopolysaccharides. Annals of the New York Academy of Sciences 1998, 851 (1), 416-421.

Roslansky, P.F. et al., Sensitivity of Limulus amebocyte lysate (LAL) to LAL-reactive glucans. Journal of clinical microbiology 1991, 29 (11), 2477-2483.

Sakai, H. et al., Detection of lipopolysaccharide in hemoglobin-vesicles by Limulus amebocyte lysate test with kinetic-turbidimetric gel clotting analysis and pretreatment of surfactant. Journal of pharmaceutical sciences 2004, 93 (2), 310-321.

Saraf, A. et al., Quantification of ergosterol and 3-hydroxy fatty acids in settled house dust by gas chromatography-mass spectrometry: comparison with fungal culture and determination of endotoxin by a Limulus amebocyte lysate assay. Applied and Environmental Microbiology 1997, 63 (7), 2554-2559.

Sifferlin, A. 351,000 People Die of Food Poisoning Globally Every Year. http://time.com/3768003/351000-people-die-of-food-poisoning-globally-every-year/ (2014).

Silverman, M.H. et al., Bacterial endotoxin in human disease. XOMA (US) LLC, Berkeley, CA, USA 1999.

Smulders, S. et al., Contamination of nanoparticles by endotoxin: evaluation of different test methods. Part Fibre Toxicol 2012, 9 (1), 41-41.

Sousa, E. et al., Quantification of endotoxins in infected root canals and acute apical abscess exudates: monitoring the effectiveness of root canal procedures in the reduction of endotoxins. Journal of endodontics 2014, 40 (2), 177-181.

Taylor, N., The FDA and USP have expanded their collaboration to ensure the quality of medicines by modernising tests and standards.

(56) References Cited

OTHER PUBLICATIONS http://www.in-pharmatechnologist.com/Processing/FDA-USP-extend-relationship-to-modernise-drug-quality (2014).
Van de Weg, C.A. et al., Lipopolysaccharide levels are elevated in dengue virus infected patients and correlate with disease severity. Journal of Clinical Virology 2012, 53 (1), 38-42.
Chałupniak, A. et al., 2014. Application of quartz tuning forks for detection of endotoxins and Gram-negative bacterial cells by monitoring of Limulus Amebocyte Lysate coagulation. Biosensors and Bioelectronics 58, 132-137.
Guo, Y.B. et al., 2010. Real-Time Biomolecular Binding Detection Using a Sensitive Photonic Crystal Biosensor. Anal. Chem. 82, 5211-5218.
Guo, Y.B., et al., 2008. Sensitive molecular binding assay using a photonic crystal structure in total internal reflection. Optics Express 16(16), 11741-11749.
Hoa, X.D. et al., 2007. Towards integrated and sensitive surface plasmon resonance biosensors: A review of recent progress. Biosensors & bioelectronics 23(2), 151-160.
Homola, J., 2003. Present and future of surface plasmon resonance biosensors. Anal Bioanal Chem 377(3), 528-539.
Homola, J., 2008. Surface plasmon resonance sensors for detection of chemical and biological species. Chemical Reviews 108(2), 462-493.
Inoue, K.Y. et al., 2012. Development of an electrochemical Limulus amebocyte lysate assay technique for portable and highly sensitive endotoxin sensor. Innate immunity 18(2), 343-349.
Liu, T et al., 2017. A quartz crystal microbalance sensor for endotoxin assay by monitoring limulus amebocyte lysate protease reaction. Anal Chim Acta 961, 106-111.
Muramatsu, H., et al., 1988. Viscosity monitoring with a piezoelectric quartz crystal and its application to determination of endotoxin by gelation of limulus amebocyte lysate. Analytica Chimica Acta 215, 91-98.
Obayashi, T., et al., 1995. Plasma $(1\rightarrow 3)$-$\beta$-D-glucan measurement in diagnosis of invasive deep mycosis and fungal febrile episodes. The Lancet 345(8941), 17-20.
Ren, K., Zheng et al., 2010. Soft-Lithography-Based High Temperature Molding Method to Fabricate Whole Teflon Microfluidic Chips. 14th International Conference on Miniaturized Systems for Chemistry and Life Sciences, Oct. 3-7, 2010 p. 554-556.
Saitô, H. et al., 1991. Relationship between conformation and biological response for $(1\rightarrow 3)$-$\beta$-d-glucans in the activation of coagulation Factor G from limulus amebocyte lysate and host-mediated antitumor activity. Demonstration of single-helix conformation as a stimulant. Carbohydrate Research 217, 181-190.
Su, W. et al., 2015. Methods of Endotoxin Detection. Journal of laboratory automation, 2211068215572136.
Zhang, B. et al., 2013. Detection of anthrax lef with DNA-based photonic crystal sensors. J Biomed Opt 16(12), 127006.
Zhang, B. et al., 2013. Label-free detection of cardiac troponin I with a photonic crystal biosensor. Biosensors & bioelectronics 58, 107-113.
Zhang, B. et al., 2013. Detection of Myoglobin with open-cavity and label-free photonic crystal biosensor. Journal of Medical Engineering, 808056.
Zhang, B. et al., 2016. Study of the Interactions of Fusarium virguliforme Toxin FvTox1 with Synthetic Peptides by Molecular Simulations and a Label-Free Biosensor. Anal Chem 88(6), 3024-3030.

\* cited by examiner

LIMULUS AMOEBOCYTE LYSATE ASSAY AND METHOD OF SAME

CROSS-REFERENCE TO RELATED APPLICATIONS

This application claims benefit from U.S. Provisional Ser. No. 62/573,535 filed Oct. 17, 2017, the contents of which are incorporated by reference in their entirety, as if fully restated herein.

BACKGROUND OF THE INVENTION

Almost since its discovery, Limulus Amoebocyte Lysate (LAL) testing has been an important part of the pharmaceutical and food industry quality control toolkit. It allows for in vitro endotoxin testing to judge pyrogenicity of test samples, thus leading to a less expensive and faster test of parenteral pharmaceuticals and medical devices that contact blood or cerebrospinal fluid (Hartung 2015). For more than 30 years, the United States Food and Drug Administration (FDA) has accepted the use of a LAL test for endotoxins in lieu of the rabbit pyrogens test that had been previously employed.

Three different endotoxin detection methods are currently used: gel-clot, turbidimetric, and chromogenic approaches. Each approach suffers from its own limitations. Thus, there is a growing demand to further increase the LAL test sensitivity, reduce the assay time and eliminate the necessity to incubate the samples involved in the reaction.

When pharmaceutical products contaminated with pyrogen are injected into the human body, they will give rise to a rapid increase in core body temperature followed by extremely rapid and severe shock, which may cause death in certain situations before the problem is even diagnosed. Therefore, it is critically important to have strict quality control on pharmaceutical products via accurate testing for pyrogenic substances. As the most common source of pyrogen, lipopolysaccharide (LPS) is a naturally occurring endotoxin, coming from a structural component of Gram-negative bacteria cell membranes. LPS is a very stable molecule, and it is difficult to remove from fluids or medications. In fact, the only possible ways to remove the pyrogenic effects of LPS are to either denature it by high heat (250° C. for 30 minutes, 200° C. for 1 hour) or treat with strong acids or bases, or hydrogen peroxide. Low pressure plasma sterilization, which has brought significant advances to laboratory equipment decontamination, does not adequately reduce the pyrogen load on a surface or a pharmaceutical product (Moisan et al. 2001). In addition to the pharmaceutical industry, detection of endotoxin is also important for the food industry. A 2010 study by the World Health Organization (WHO) revealed that worldwide, there were 351,000 deaths and 582 million cases of food-borne diseases. Of those deaths, 89,000 were caused by two gram-negative bacterial strains, *E. coli* and *Salmonella*. Proper test of industrialized food productions for these gram-negative bacteria can minimize the likelihood of contamination and therefore save lives.

LAL endotoxin testing is approved for testing drugs, products and medical devices that come in contact with the blood or cerebrospinal fluid. It is one of the few methods approved by the United States Pharmacopeia and FDA as an acceptable endotoxin testing strategy for oral and injectable medications, as well as implantable devices such as hip replacements, artificial hearts, and man-made ligaments (Taylor 2011). LAL testing has also been employed in a wide variety of studies: testing bacterial growth in Glaciers (Barnett et al. 2012), testing for the presence of pyrogens in nanoparticle fluids (Smulders et al. 2012), verifying safe work environments in ranching and farming (Basinas et al. 2015), and observing that there are endotoxin and $(1\rightarrow3)$-$\beta$-D-glucan (a component of fungal cell walls) fluctuations with each season (Hwang et al. 2014).

The most important use of the LAL test, to date, is the testing of pharmaceutical contamination by gram-negative bacteria. LAL is an aqueous extract of blood cells (amoebocytes) from the horseshoe crab, which reacts with bacterial endotoxin or lipopolysaccharide (LPS) and results in a semi-solid mass (coagulation) due to a clotting factor contained in LAL. This reaction is the basis of the three conventional LAL test methods, i.e., gel-clot, turbidimetric, and chromogenic approaches. LAL testing based on a gel clot method may give a qualitative result on bacterial endotoxin. The LAL gel clot reaction is a multi-step enzymatic reaction which is initiated by the addition of the fluid of interest into the LAL assay solution in a 1:1 ratio. The endotoxin which may be in the fluid of interest then binds to Factor C reagent (it has also been shown that the endotoxin binds to both Factor C and B initially)(Kobayashi et al. 2015) which then activates Factor B, which then activates the proclotting enzyme and cleaves the coagulogen protein, resulting in the gelation of the mixed solution. The gel clot assay is run in a tube containing a testing solution mixed with LAL reagents. After a one-hour incubation period at 37° C., the tube is flipped upside down. A firm clot that stays in the bottom of the tube indicates the presence of endotoxin, whereas the result is negative for endotoxin if liquid flows down the side of the tube.

In addition to the gel clot test, there are two quantitative, kinetic LAL assays commercially available. The turbidimetric assay uses the same enzymatic cascade as the gel clot test, but adds a turbidity scanner to detect the change in scattered light over the whole reaction sequence, rather than only at the end-point. A test sample is first mixed with LAL reagents and the change in its turbidity with time is then monitored. If endotoxin is present in the sample, the solution becomes cloudy or turbid and the time required for the change in turbidity is inversely proportional to the amount of endotoxin present. The other kinetic assay is termed a chromogenic test, where the manufacturer switches the coagulogen in the final step of the enzymatic cascade with a chromogenic substrate. A test sample is mixed with LAL reagents and the solution becomes yellow in the presence of endotoxin due to the process of cleaving the chromogenic substrate by the activated clotting enzyme. Each of these conventional LAL test methodologies have limited detection sensitivity and speed and are not suitable for samples containing certain inhibitors.

Current LAL assays all have their limitations in detection sensitivity, with the best commercial LAL assay sensitivity of 0.005 EU/mL, which equates to 0.0005 ng/mL to 0.001 ng/mL for most bacterial endotoxins (Kobayashi et al. 2015). The current approaches for LAL test are also time consuming, with a typical assay time of one hour. In addition to the limitations in detection sensitivity and speed, another major limiting factor of the LAL test is that it is a protease reaction. Protease inhibitors, anti-coagulation molecules (blood thinners), and LPS sequestration compounds (high-density lipoprotein, albumin, heparin, anti-endotoxin antibodies, bacterial permeability increasing protein, and EDTA) can greatly impact the sensitivity of conventional LAL assays.

LAL pyrogen testing fills a sizeable need in today's world (Hartung 2015). The costs of endotoxin testing have been estimated by Markets-and-Markets to be over $823 million in 2019, with a Compound Annual Growth Rate of 12.23% for the foreseeable future (Hartung 2015).

The detection of LPS by the LAL assay is a proxy for how the human body reacts to pyrogens. The horseshoe crab's immune response causes gelation of its blood, but the immune response in humans is inflammation and fever. Because of the inherent complexity of the human body's reaction to a specific molecule or class of molecules, testing for the presence of the chemical makeup of that molecule (i.e. through Gas Chromatograph tests) often leads to false positives or false negatives (Saraf et al. 1997). Even the LAL test itself is not a foolproof way of testing for pyrogenicity in the human body, as the LAL recognition of certain classes of LPS is much stronger than it would be in the human body. Additionally, humans have a pyrogenic reaction to some types of gram positive bacteria, and the LAL test does not react to these (Hartung 2015; Saraf et al. 1997). Even with its limitations, the LAL test is the gold standard for testing for pyrogenicity. It has been used to test a variety of conditions, such as Sepsis treatments (Silverman and Ostro 1999), refining root canal drug delivery strategies (de Oliveira et al. 2012; Marinho et al. 2015), root canal procedure strategies (Sousa et al. 2014), and early indicators of intestinal membrane breakdown in Dengue Fever patients (van de Weg et al. 2012). Due to the limitations of the current LAL test, as well as the large market share of endotoxin testing, refinements of pyrogen tests are constantly being made, including using Quartz sensors (Chalupniak et al. 2014; Liu et al. 2017); electrochemical feedback sensors (Inoue et al. 2012); nanoparticle suspensions (Li et al. 2015); piezoelectric sensors (Muramatsu et al. 1988); and SPR sensors (Su and Ding 2015). In addition, alternative pyrogen test compounds are constantly being engineered, such as the beta glucan only test, GLUCATELL (Obayashi et al. 1995), the Monoclonal Antibody Test (MAT) (Hartung 2015; Sander et al. 2008), recombinant Factor C (Barnett et al. 2012), and nano-molecular imprinted polymers (MIP) (Su and Ding 2015). However, each has inherent problems that result in them not being as sensitive or specific as the LAL test.

The present invention attempts to solve these problems as well as others.

SUMMARY OF THE INVENTION

In accordance with the present invention there is provided a new approach to enhance LAL testing and avoid the limitations of conventional LAL testing methodologies. The present invention provides both a system and method based upon a photonic-crystal biosensor optimized for LAL testing. When employing the inventive system and method, LAL test sensitivity has been increased over two orders of magnitude over the conventional testing methodologies and the testing duration has been reduced by at least 50 percent over the conventional testing methodologies, all while conducting the LAL assay at room temperature.

In accordance with the present invention, the novel use of a photonic crystal-total internal reflection (PC-TIR) biosensor in an LAL assay is employed to achieve rapid and ultrasensitive results. Different from the conventional methodologies, the present invention employs a photonic crystal-total internal reflection (PC-TIR) biosensor for LAL testing. The PC-TIR allows the inventive system to achieve rapid and ultrasensitive assay results even in the presence of certain inhibitors. The LAL assays with a PC-TIR biosensor is based on the detection of the refractive index (RI) of a test solution, as the refractive index changes during the LAL assay in the presence of endotoxin.

The inventive PC-TIR biosensor used possesses a unique open optical microcavity. A conventional optical microcavity may result in a sharp resonant condition by having a cavity layer sandwiched by two pieces of PC structures. However, this conventional, closed configuration is not suitable for biosensing as it is very difficult to place analyte solutions at the sensing layer (cavity layer). For real-time bioassays, the present invention employs an open microcavity structure. The open microcavity structure opens the closed microcavity structure by splitting the cavity layer through the middle and employing only half of the structure in a total internal reflection (TIR) configuration. There is a mirror image of the PC structure due to TIR. A microcavity can therefore still be formed between the PC structure and its mirror image. This unique configuration forms a PC-TIR biosensor with an open sensing surface, which allows the biosensor directly exposed to the analyte solutions for real-time bioassays. A sharp resonant dip (~1 nm) can be achieved with a PC-TIR biosensor, which facilitates rapid and sensitive LAL assays by accurately monitoring the change in the sharp resonant condition of the open microcavity affected by the changes in the refractive index of the analyte solutions.

DETAILED DESCRIPTION OF THE PREFERRED EMBODIMENTS

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Biosensor Chip Preparation

Figure 1:
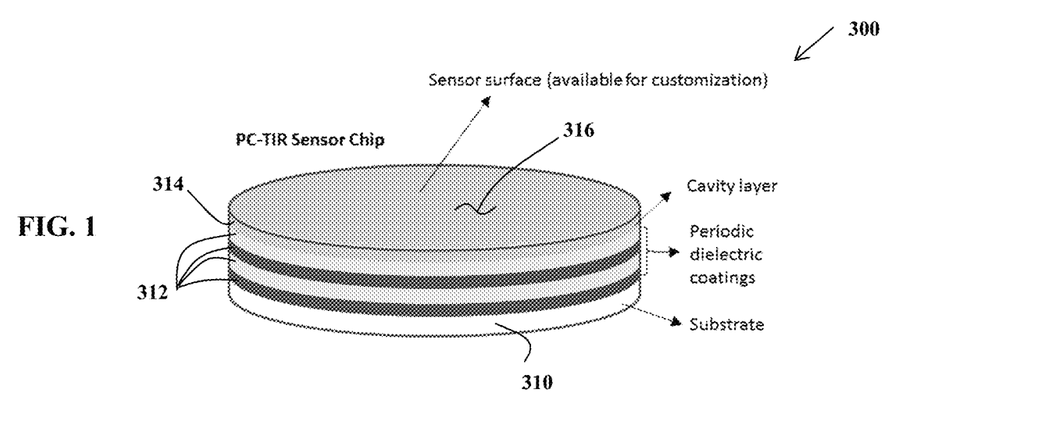
FIG. 1 is a schematic of the PC-TIR sensor for LAL assays.

In accordance with the best mode contemplated for the present invention, the PC-TIR biosensor employed in the present invention has an open optical microcavity and is based upon the PC-TIR biosensor described in U.S. Pat. No. 7,639,362, which is herein incorporated by reference in its entirety. The inventive PC-TIR biosensor was designed based on numerical simulations with a transfer matrix approach and fabricated with electron-beam physical vapor deposition. As shown in FIG. 1, the inventive PC-TIR biosensor 300 has a plurality of alternating layers 312 of titanium dioxide and silicon dioxide coated on a glass substrate 310. In accordance with an illustrative embodiment, each $TiO_2$ layer is about 91 nm in thickness, each $SiO_2$ layer is about 309 nm in thickness and a glass substrate is BK-7 optical glass. A cavity layer 314 was formed above the plurality of alternating layers and was formed with about 382 nm silica and about 8 nm of silicon. A thin silicon layer gives rise to an appropriate level of absorption such that a sharp dip in the reflectance spectrum is introduced at the resonant wavelength of an open optical microcavity or open cavity formed when the PC structure is used in a TIR configuration (Ye et al. 2013; Ye et al. 2009). When the RI of analyte solutions on top of the PC-TIR biosensor surface changes, the resonant wavelength shifts accordingly. Sample or Analyze wells or microfluidic channels (223 in FIG. 3) can be attached to or formed in the top surface 316 of the PC-TIR sensor 300 for sample handling, which may be formed using a polydimethylsiloxane (PDMS) replica molding process according to one embodiment. PDMS base and curing agents (SYLGARD184, Dow Corning) were mixed at a ratio of about 10:1. The mixture was degassed in a vacuum chamber for about 10 minutes and then cast on a mold and cured at room temperature. To bind the sample wells with the biosensor chip, the surface of a PC-TIR biosensor chip and the PDMS sample well were first processed with a plasma cleaner (Harrick Plasma) for about 60 seconds, which renders the surface hydrophilic. The silanol (SiOH) groups created on the surface form bridging Si—O—Si bond when the oxidized PDMS surface was placed in contact with the biosensor chip surface, creating an irreversible seal. The PC-TIR biosensor chip together with the sample wells were baked at 200° C. for 1 hour before usage to remove any possible contaminations.

Biosensor Apparatus

Figure 2:
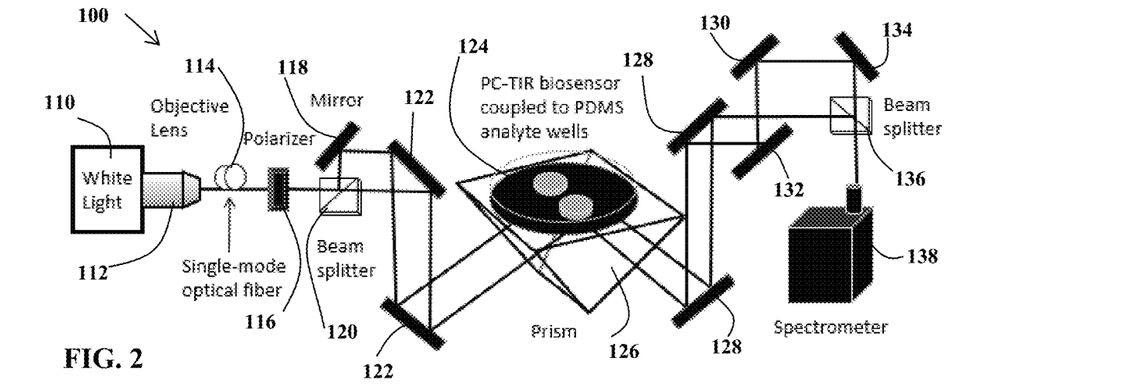
FIG. 2 is a schematic of the inventive PC-TIR sensor based LAL assay system in spectroscopy detection mode.

The inventive LAL assay system 100 in spectroscopy detection mode, as depicted in FIG. 2, was used to sensitively detect the changes in RI of the LAL analyte solutions on the PC-TIR biosensor 222. White light produced by a fiber illuminator 110 (Thorlabs OSL1) as the light source was coupled into a single-mode optical fiber 114 for transmitting light, and S-polarization was selected with a polarizer 116 before the beam was split into two using a beam splitter 120 and mirrors 118. The polarized light then passed with mirrors 122 to the biosensor 124 mounted on an optically transparent prism 126, the biosensor 124 was oriented in a TIR configuration and the reflectance spectra of the two optical paths from the biosensor were detected with a high-resolution spectrometer 138 (Ocean Optics HR 4000). Readings were taken via the Ocean View software package (Ocean Optics) and recorded as full spectrum data files every 30 seconds. Each spectrum consisted of the average of ten 0.1 second scans with boxcar smoothing with a radius of about 2.

Figure 3:
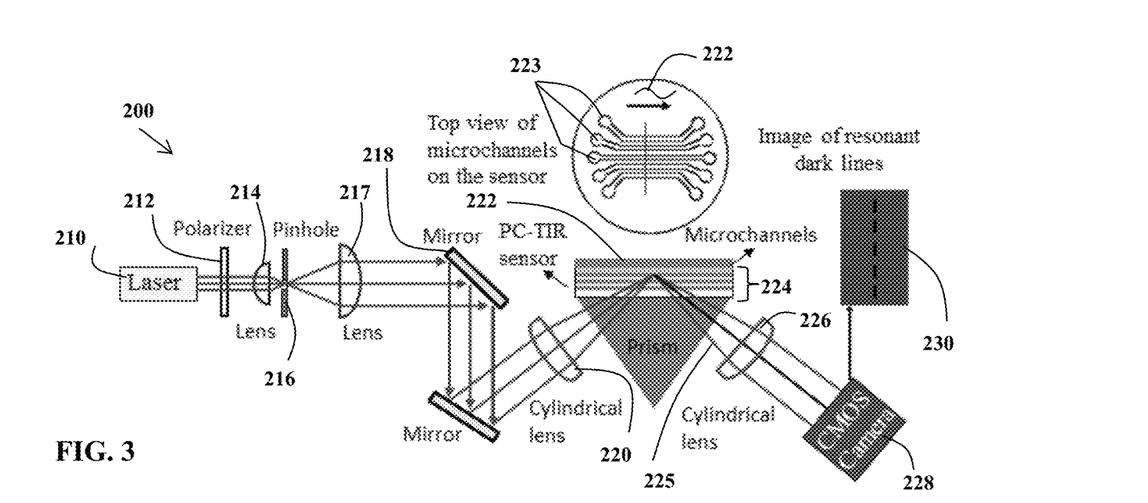
FIG. 3 is a schematic of the inventive PC-TIR sensor based LAL assay system in angular detection mode.

The inventive LAL assay system 200 may be utilized in angular detection mode, as shown in FIG. 3. For this embodiment, a laser 210 is the laser light source, such as a Helium-Neon laser, and is used as a probe light to monitor changes in the resonant condition of the PC-TIR biosensor 222 due to reaction of LAL reagents with endotoxins. The laser light source transmits a laser light beam, which first goes through a polarizer 212 to select s-polarization for the sensor mounted on a prism. The polarized laser light beam then passes through a spatial filter composed of a pinhole 216 and a pair of lenses 214, 217 to obtain a high quality spatial mode and expand the laser light beam 219, preferably to about 10 mm. Two mirrors 218 were used to direct the laser light beam 219 towards the PC-TIR biosensor 222 coupled to an optical prism, preferably with index matching oil. A cylindrical or collimating lens 220 is used to focus the laser light beam 219 into a line crossing a plurality of microchannels 223 on the PC-TIR biosensor 222 surface. The reflected laser light beam 225 is collimated with another cylindrical lens 226 and an imaging device 228 images the collimated reflected laser light beam, which may be a CMOS camera in one embodiment. A plurality of short sections of dark lines appear on the image 230, which correspond to the number of the plurality of microchannels 223 and the resonant angle of the probe beam 219 for the microchannels 223 on the PC-TIR biosensor 222. The positions of the dark lines sensitively shift due to the change of refractive index of the test samples in the microchannels when LAL reagents react with endotoxins in the samples.

Limulus Amoebocyte Lysate (LAL) and Endotoxin Preparation

In one embodiment, an LAL reagent KTA2 (Charles River, lot D2161L, 0.005 EU/mL sensitivity) was used. KTA2 is a kinetic turbidimetric reagent. The directions for proper rehydration and preparation included in the LAL reagent package were followed. The control standard endotoxin (Charles River, CSE, Catalog #E120) was employed. Solutions of 0.05 EU/mL, 0.0025 EU/mL, 0.00025 EU/mL, and 0.000025 EU/mL were made by dissolving the appropriate weight of endotoxin in LAL reagent water (LRW) (Charles River), according to the CSE instructions.

Measurement Procedure

After the appropriate dilutions of CSE were made and LAL reagents were rehydrated, the baked biosensor was placed on an equilateral prism with index matching fluid and about 150 μl of LRW was first added into both sample or analyte wells on the biosensor. Alignment of the optical beam path reflected from the biosensor was conducted to couple the probe beam into a high-resolution spectrometer, so that resonant dips appeared at the correct wavelength in the reflectance spectrum of the biosensor. The LRW was then replaced with about 150 μl of rehydrated Lysate in the sample wells of the biosensor. Next, 150 μl LRW was added into one well and the timer was started to record data in about 30 second increments, while about 150 μl of the endotoxin sample was added into the other well. Detection of the spectrum of the reflected beams from the two wells was switched every thirty seconds, so that the spectrometer measured the spectra of both wells every minute. Each run was monitored for about 20 minutes. After the assay, the sample wells and the biosensor chip were cleaned first with acetone, and then with deionized water, and dried with compressed air to assure no fluid solution remained on the biosensor surface. In order to reuse the biosensor, the cleaned biosensor chip together with the sample wells were baked at about 200° C. on a hot plate or in an oven for at least one hour in an aluminum enclosure, to ensure even heat transfer, and to restrict room air contamination.

Triplicates of all solutions were run to make statistical analysis possible. Because each data point consisted of the average of about 10 spectral samples, the standard error was selected as the appropriate error bar in figures showing run results. Standard deviation and the coefficient of variation were also calculated using Excel. Adjusted R-square values were used to judge the goodness of fit for the time-dependent data of the resonant wavelength shifts of a PC-TIR biosensor. Biosensor drift was corrected for by subtracting the $H_2O$ only data from the other data sets.

The term "statistically significant" may relate to the coefficient of determination, denoted $R^2$, which is the proportion of the variance in the dependent variable that is predictable from the independent variable(s). Thus, in this case, statistically significant resonant wavelength shifts the $R^2$, value around 0.90 and 0.99 would be statistically significant.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in °C. or is at ambient temperature, and pressure is at or near atmospheric.

Results

Figure 4:
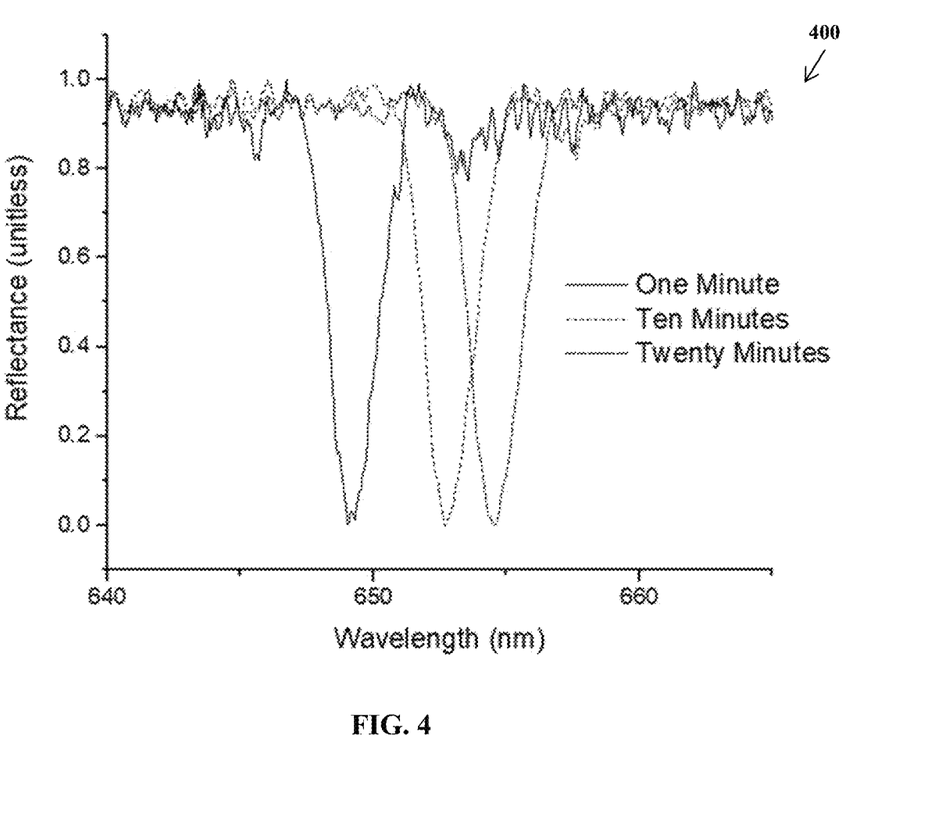
FIG. 4 shows reflectance spectra from a photonic crystal biosensor in an LAL endotoxin assay.

In previous studies PC-TIR sensors were used for molecular binding assays ranging from well-studied coupling agents to small molecule binding and nucleic acid and cardiac biomarker detection (Guo et al. 2010; Guo et al. 2008; Zhang et al. 2011; Zhang et al. 2014; Zhang et al. 2013; Zhang et al. 2016). In contrast, for the first time, the present invention utilizes the PC-TIR biosensor to monitor the changes in RI of LAL analyte solutions, which sensitively reflects the amount of endotoxin in the test samples. FIG. 4 shows several representative reflectance spectra of a PC-TIR biosensor at different time points when a LAL analyte solution was added on the biosensor surface. The sharp resonant dip shifts with time while the LAL responds to the endotoxin.

Figure 5:
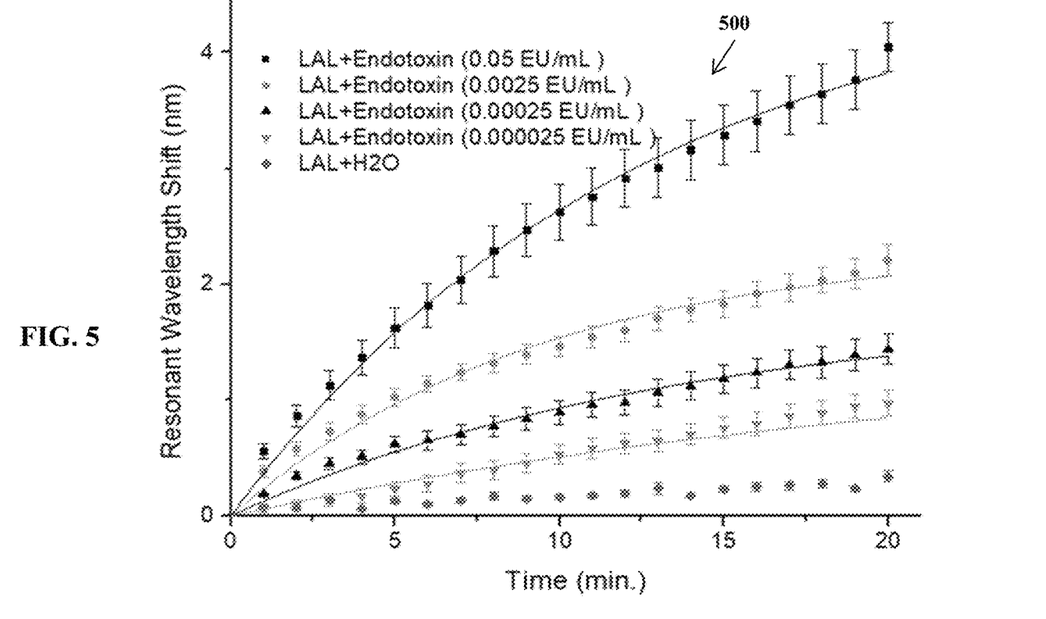
FIG. 5 is a time dependence graph of resonant dips in reflectance spectra of the PC biosensor in LAL endotoxin assays.

The wavelength shift of the resonant dip in the reflectance spectra of the PC-TIR biosensors was monitored with a high-resolution spectrometer for every minute over a 20-minute period for each sample. FIG. 4 illustrates the wavelength shift over time. The reflectance spectra were loaded into the OriginPro data analysis program by OriginLab to apply a Lorentzian curve fit and determine the center wavelength of the resonant dip. By fitting the curve rather than simply picking the lowest point of the spectrum, one can obtain a more accurate value of the resonant wavelength. The time dependence of the center resonant wavelength obtained from fitting the spectral curve is shown in FIG. 5. The results shown are for the test samples with different concentrations of endotoxin as well as the control samples. The error bars represent the standard errors of different runs. The data indicate that even the most diluted endotoxin used (about 0.000025 EU/mL) resulted in a clearly measurable difference from the negative control (LAL with $H_2O$). Based on the average pyrogenicity of endotoxin this equates approximately to about 0.0000025 ng/mL of endotoxin in the solution, which is by far the greatest sensitivity of any previously published LAL testing strategies. Given that the LAL reagent employed has a sensitivity of about 0.005 EU/mL, the system and method of the present invention demonstrates at least a 200-fold increase in detection sensitivity. This significant improvement in detection sensitivity can be attributed to the PC-TIR's capability for ultrasensitive measurements of the RI changes in the analyte solutions caused by LAL reactions to the minute amount of endotoxin. The sharp resonance bandwidth (~2 nm) of the PC-TIR biosensor shown in FIG. 4 is much narrower than a typical surface plasmon resonance (SPR) biosensor (~40 nm) (Hoa et al. 2007; Homola 2003, 2008), thus allowing precise measurements of resonant wavelength shifts for enhanced detection sensitivity.

Figure 6:
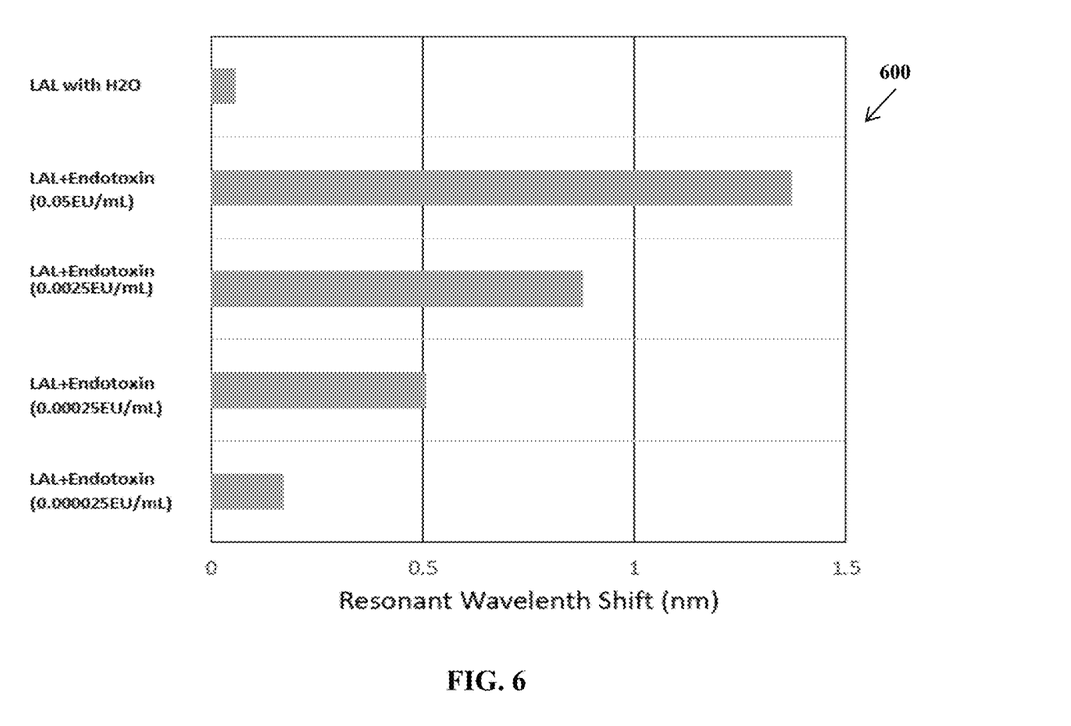
FIG. 6 is a graph of resonant wavelength shifts of a PC-TIR biosensor at five minutes in LAL assays of endotoxin with different concentrations.

In addition to the sensitivity, the time required for LAL assays is also an important consideration in industry applications for higher throughput and cost saving. To illustrate the fast response of the PC-TIR biosensor to LAL assays, the resonant wavelength shift of the biosensor has been plotted as a function of the endotoxin concentration at a selected time point-5 minutes after endotoxins were added to LAL reagents. FIG. 6 shows that the shift in the resonant wavelength of the biosensor increases with increasing the concentration of the endotoxin and within this short five minute period, all the samples with different endotoxin concentrations can already be well distinguished. This result clearly demonstrates the fast response time, another unique feature of the PC-TIR biosensor based LAL assays in addition to its ultrahigh sensitivity. It can be seen from FIG. 5 that different amounts of resonant wavelength shifts appear even as early as two minutes, although the 5-minute time point was selected for a conservative claim. In contrast, the conventional approaches, including gel clot, turbidimetric, and chromogenic assays, take much longer to generate assay results, especially for samples with low endotoxin concentrations. Gel clot assays typical take one hour, while turbidimetric and chromogenic assays also need about 15 minutes to complete one run. The fast response of the PC-TIR, even without the need for equilibrating to about 37° C., can significantly shorten the assay time, which is desired in many industry applications.

To obtain the reaction rate of the LAL assays detected with the PC-TIR biosensor, a nonlinear least squares regression was used to analyze the time dependent resonant wavelength shifts $\Delta\lambda$ of the biosensor, which can be fitted to the following first order exponential function (1)

$$\Delta\lambda = A(1 - e^{-Bt}) \quad (1)$$

where A and B are fitting parameters. The fitting curves are plotted in FIG. 5 while the fitting parameters are listed in Table 1 for test samples with different endotoxin concentrations.

Table 1. Fitting results of the time dependent resonant wavelength shifts for test samples with different concentrations of endotoxin.

| Sample | Fitting Parameters + Value | Adjusted $R^2$ |
|---|---|---|
| LAL + Endotoxin (0.05 EU/mL) | A = 4.775 ± 0.163<br>B = 0.081 ± 0.005 | 0.994 |
| LAL + Endotoxin (0.0025 EU/mL) | A = 2.355 ± 0.088<br>B = 0.106 ± 0.008 | 0.984 |
| LAL + Endotoxin (0.00025 EU/mL) | A = 1.793 ± 0.108<br>B = 0.074 ± 0.008 | 0.964 |
| LAL + Endotoxin (0.000025 EU/mL) | A = 1.537 ± 0.414<br>B = 0.040 ± 0.015 | 0.958 |

Figure 7:
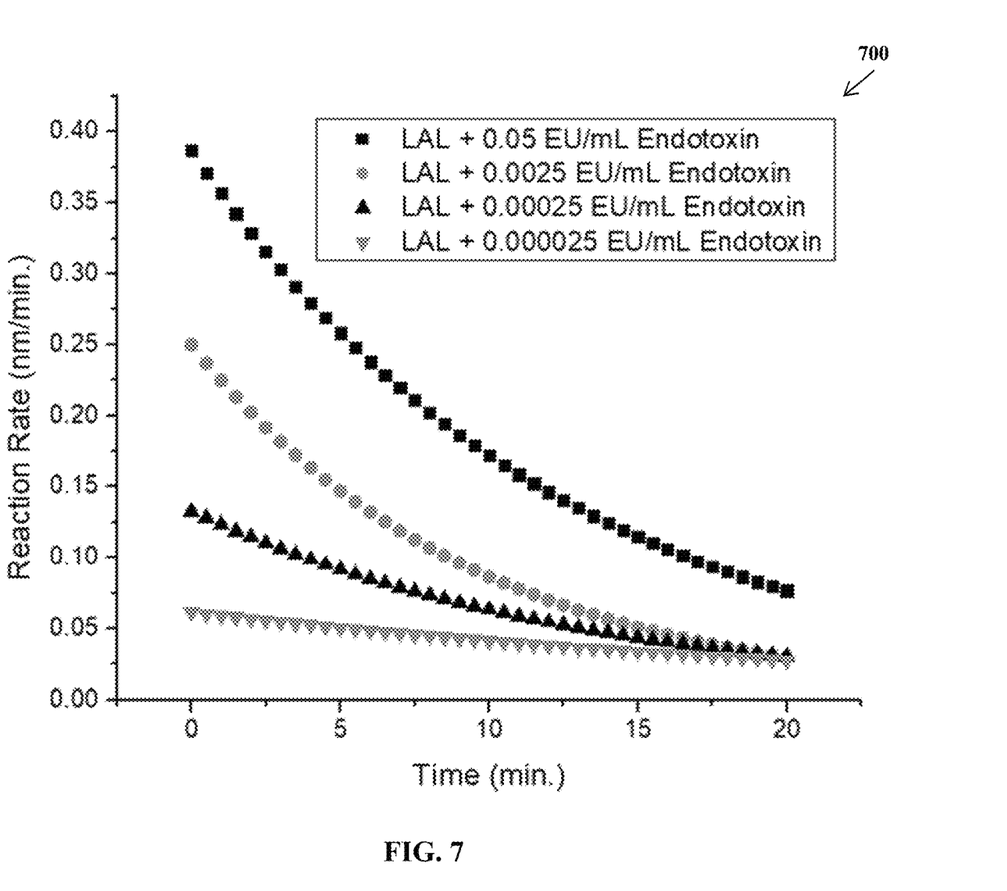
FIG. 7 is a graph of reaction rate between LAL reagents and endotoxin with different concentrations.

The adjusted R square values obtained from the fitting are close to one, which indicates the goodness of fit. By taking the derivative of Eq. (1), the reaction rate was obtained according to formula (2):

$$\text{Reaction Rate} = ABe^{-Bt} \quad (2)$$

which is plotted in FIG. 7. It can be seen that the reaction rate is generally higher for higher concentrations of endotoxin samples. Thus, the reaction rate at certain time points, for example at t=0, may also be utilized as a good parameter in addition to the resonant wavelength shifts to indicate endotoxin concentrations. Moreover, there is a general trend that the reaction rate for each sample decreases with assay time. This is reasonable as the reaction between LAL reagents and endotoxins reduces the amount of LAL reagents or free endotoxins and slows down the reaction.

It has also been found that in addition to using LAL reagents, extracts from LAL reagents that include purified Factor C and/or recombinant Factor C (rFC) may be employed with the present invention. LAL testing may not include protease amplifying steps, thereby necessitating higher sensitivity biosensor be employed. The increased sensitivity of the PC-TIR biosensor in the present system and method, relative to that of conventional LAL assay systems and methods, addresses this need for higher sensitivity.

The inventive system and method demonstrate that an LAL assay that measures the refractive index of a test solution using a photonic crystal biosensor offers significantly enhanced sensitivity together with substantially faster discrimination of positive and negative results. The PC-TIR biosensor chips can be reused as they are robust through a number of heat cycles. This improvement can be attributed to the new detection principle based on a PC-TIR biosensor for sensitive monitoring of RI changes in the analyte solutions, which is fundamentally different from other conventional methods of LAL assays. In addition, the PC-TIR biosensor has a simple 1-dimensional (1D) PC structure, which is basically a multi-layered dielectric coating and can be easily fabricated with well-established vacuum deposition techniques. In contrast to 2D or 3D PC structures, the simplicity of the PC-TIR biosensor structure allows for low-cost reproduction, robust performance, and ultrahigh sensitivity assays, which are important factors for potential commercialization of this unique technique for sensitive and rapid LAL assays.

Furthermore, there is promise in testing samples that possibly have confounding variables via extreme dilution due to the fact the LAL assays on a PC-TIR chip have a very high sensitivity. Future research is needed in this area, and a more complete list of confounding molecules can be tested with the PC-TIR chip with the endotoxin standard, blood plasma, and other analytes of interest. A method for binding the LAL proteins to the biosensor surface in conjunction with a microfluidic system may further lead to lower volumes of LAL needed to test solutions for pyrogenicity.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

We claim:

1. A Limulus Amoebocyte Lysate (LAL) assay system comprising a photonic crystal total internal reflection (PC-TIR) biosensor that measures endotoxins in an analyte by monitoring changes in a refractive index of the analyte, wherein the PC-TIR biosensor has a plurality of microchannels on a surface thereof; and
   a laser light source providing a laser light beam;
   a polarizer positioned to receive the laser light beam from the laser light source;
   a spatial filter configured to receive a polarized laser light beam from the polarizer and expand the polarized laser light beam;
   a plurality of mirrors configured to direct the expanded polarized laser light beam toward the PC-TIR biosensor;
   a lens configured to focus the expanded polarized laser light beam into a line crossing at least one of the plurality of microchannels on the surface of the PC-TIR biosensor;
   a collimating lens positioned to receive a reflected laser light beam from the surface of the PC-TIR biosensor; and
   an imaging device capable of imaging the collimated reflected laser light beam to create an image, the image having a plurality of sections corresponding to a resonant angle of the laser light beam.

2. A Limulus Amoebocyte Lysate (LAL) assay method wherein a refractive index of an analyte suspected of containing an endotoxin is measured, comprising the steps of:
   a. Placing the analyte in an evanescent field of a photonic crystal biosensor having an open cavity and total internal reflection and a plurality of microchannels on a surface thereof;
   b. Providing a source of polarized laser light directed to the photonic crystal biosensor, expanding the polarized laser light and focusing the expanded polarized light into a line;
   c. Passing the line of laser light through the analyte and crossing at least one of the plurality of microchannels on the surface of the photonic crystal biosensor;
   d. Imaging reflected laser light, the image having a plurality of sections corresponding to a resonant angle of the laser light beam; and
   e. Measuring changes in the refractive index of the analyte suspected of containing the endotoxin.

3. The LAL assay method of claim 2, further comprising the step of beam splitting the polarized light prior to the step of passing the light through the analyte.

4. The LAL assay method of claim 2, further comprising the step of providing an LAL reagent.

5. The LAL assay method of claim 4, wherein the LAL reagent selected comprises Factor C reagent, and wherein the Factor C reagent selected comprises recombinant Factor C.

6. The LAL assay system of claim 1, further comprising at least one analyte well associated with the PC-TIR biosensor.

7. The LAL assay system of claim 6, further comprising a prism for transmitting light to the PC-TIR biosensor and passing the light from the PC-TIR biosensor to a spectrometer for receiving the transmitted light.

8. The LAL assay system of claim 1, further comprising:
   a beam splitter optically coupled to the polarizer;
   a prism optically coupled to at least one of a plurality of analyte wells associated with the PC-TIR biosensor; and
   a spectrometer optically coupled to the prism.

* * * * *